United States Patent [19]

Hardy et al.

[11] Patent Number: 4,697,030

[45] Date of Patent: Sep. 29, 1987

[54] PHOSPHATE-CONTAINING AND PHOSPHONATE-CONTAINING PHOSPHATE ESTERS

[75] Inventors: Thomas A. Hardy, Thousand Oaks, Calif.; Edward N. Walsh, New City, N.Y.

[73] Assignee: Stauffer Chemical Company, Westport, Conn.

[21] Appl. No.: 737,374

[22] Filed: May 23, 1985

[51] Int. Cl.$^4$ .............................. C07F 9/11; C07F 9/40
[52] U.S. Cl. ...................................... 558/163; 558/164
[58] Field of Search ................................ 558/163, 164

[56] References Cited

U.S. PATENT DOCUMENTS

| | | | |
|---|---|---|---|
| 2,909,559 | 10/1959 | Lanham | 558/164 |
| 3,391,226 | 7/1968 | Birum et al. | 558/163 |
| 3,433,856 | 3/1969 | Friedman | 558/163 |
| 3,525,705 | 8/1970 | Harowitz | 558/164 |

*Primary Examiner*—Anton H. Sutto

[57] ABSTRACT

There are disclosed multiphosphorus-containing compounds comprising phosphonate-containing or phosphate-containing phosphate esters. The compounds can be prepared by: (a) reacting a phosphonate-containing or phosphate-containing alcohol with phosphorus pentoxide following by reaction with an epoxide, (b) reacting a phosphonate-containing or phosphate-containing alcohol with a phosphorus oxyhalide, hydrolyzing any phosphorus halogen bonds and then reacting the resulting phosphoric acid derivative with an epoxide, (c) transesterifying a phosphonate-containing or phosphate-containing alcohol with a dialkyl phosphite, oxidizing the resulting compound to yield a phosphoric acid derivative and reacting the phosphoric acid derivative with an epoxide. The compounds are useful as flame retardant additives for polyurethanes and textiles.

18 Claims, No Drawings

PHOSPHATE-CONTAINING AND PHOSPHONATE-CONTAINING PHOSPHATE ESTERS

FIELD OF THE INVENTION

The present invention relates to a novel class of phosphate-containing or phosphonate-containing phosphate esters. The present invention also relates to methods for the preparation of these compounds and the use of these compounds as flame retardant additives.

BACKGROUND OF THE INVENTION

In today's modern technology, phosphorus compounds play an increasingly important role. These compounds find utility as flame retardant additives for plastics and textiles, lubricant additives, biocides, herbicides, insecticides, pesticides, fungicides, growth regulators, ore flotation agents and metal plating additives.

Various classes of phosphorus derivative compounds are known.

U.S. Pat. No. 3,042,701 discloses phosphorus compounds having a plurality of pentavalent phosphorus ester radicals. The compounds disclosed in the above patent are selected from the class consisting of phosphate diesters and phosphate-containing polyesters. The pentavalent state is achieved by the oxidation or thionation of the phosphite-phosphonate intermediates to phosphate-phosphonates.

U.S. Pat. No. 2,372,244 discloses a process for the preparation of what the inventors believe to be "analogs of the alkylene glycol substituted partial esters of the acids of phosphorus".

U.S. Pat. No. 3,525,705 discloses a method for the production of fire resistant polyurethane products. In the method disclosed in the above patent, an organic polyisocyanate is reacted with the reaction product of the monoester of phosphoric acid, a mono or diester of diphosphoric acid, or a mono or diester of pyrophosphoric acid and an epoxide.

U.S. Pat. No. 2,909,559 discloses a process for producing hydroxyl-containing polymeric phosphate esters by heating a hydroxyl-containing phosphate ester of the structure:

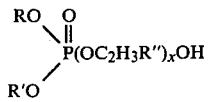

to a temperature of from about 90° C. to about 250° C.

SUMMARY OF THE INVENTION

The present invention is directed to organophosphorus compounds having the formula:

wherein

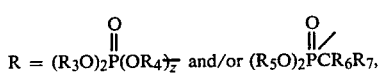

$R_1$, $R_3$ and $R_5$ are the same or different and are alkyl, haloalkyl, aryl or haloaryl groups of from 1 to about 20 carbon atoms, $R_6$ and $R_7$ are the same or different and are hydrogen, alkyl, haloalkyl, aryl or haloaryl groups of from 1 to about 20 carbon atoms, $R_2$ and $R_4$ are the same or different and are alkylene or haloalkylene of from 2 to about 10 carbon atoms, n is an integer from 1 to 2, a can be 0 or 1, y is an integer from 1 to 10, and z is an integer from 1 to 10 with the proviso that n+a must equal 2.

The compounds of the present invention may be produced by a number of processes.

In one embodiment of the present invention, a phosphate-containing or phosphonate-containing alcohol is reacted with phosphorus pentoxide, with or without an organic solvent. The resulting product is then reacted with an epoxide to yield the desired product.

In another embodiment, a phosphate-containing or phosponate-containing alcohol is reacted with a phosphorus oxyhalide in the presence of a Lewis acid catalyst followed by hydrolysis of any remaining phosphorus halogen bonds to yield a phosphoric acid derivative. The phosphoric acid derivative is then reacted with an epoxide to yield the desired product.

In yet another embodiment of the present invention, a phosphate-containing or phosphonate-containing alcohol is transesterified with a dialkyl phosphite. In this reaction, the phoshpate-containing or phosphonate-containing alcohol replaces one or two simple alkyl groups. The resulting phosphite is then oxidized to a phosphoric acid derivative by oxygen with, for example, nitrogen dioxide. The resulting phosphoric acid derivative is then treated with an epoxide to yield the desired product.

Another embodiment of the present invention comprises the use of the novel compounds of the present invention as flame-retardant additives.

In one embodiment, the novel compounds, in combination with a flexible polyurethane foam, produce a flame-retardant flexible foam compound.

In another embodiment, these compounds, in combination with a rigid polyurethane foam, produce a rigid foam compound having improved flame-retardant properties.

In yet another embodiment, the novel compounds of the present invention, when copolymerized with melamine derivatives, produce textile products having improved flame-retardant properties.

Other objects, features, and advantages of the present invention will become more apparent from the Detailed Description of the Invention which follows.

DETAILED DESCRIPTION OF THE INVENTION

The novel compounds of the present invention are represented by the formula:

wherein

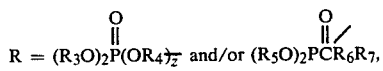

$R_1$, $R_3$, and $R_5$ may be the same or different and are alkyl, haloalkyl, aryl, or haloaryl, $R_6$ and $R_7$ may be the same or different and are hydrogen, alkyl, haloalkyl, aryl, or haloaryl, $R_2$ and $R_4$ may be the same or different and are alkylene and haloalkylene, n is an integer from 1 to 2, a can be 0 or 1, y is an integer from 1 to 10 and z is an integer from 1 to 10. Preferably, the alkyl, haloalkyl, aryl, and haloaryl groups contain from 1 to about 20 carbon atoms, and the alkylene and haloalkylene groups contain from 2 to about 10 carbon atoms.

The compounds of the present invention may be prepared by a variety of methods.

In one method, a phosphate-containing or phosphonate-containing alcohol, represented by the general formula ROH wherein R is as defined previously, is reacted with phosphorus pentoxide, with or without an organic solvent. This reaction can be expressed as:

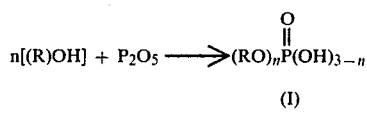

(I)

wherein compound I is produced. Compound I is then reacted with an epoxide, represented by the general formula $_yR_2{=}O$ wherein y and $R_2$ are as previously described, in a reaction which can be expressed as follows:

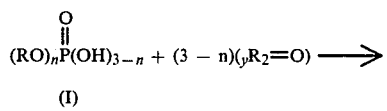

(I)

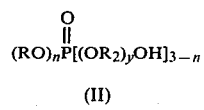

(II)

Product II, thus obtained, may be referred to, when n is 1 or 2, as a multiphosphorus-containing phosphate ester.

In another embodiment, a phosphate-containing or phosphonate-containing alcohol, represented by the general formula ROH wherein R is as defined above, is reacted with a phosphorus oxyhalide, represented by the general formula $POX_3$ wherein X is a halogen, i.e., chlorine or bromine, in the presence of a Lewis acid catalyst in a reaction which can be expressed as follows:

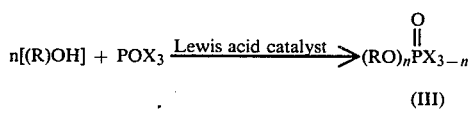

(III)

Product III, a halogenated phosphate or phosphonate derivative, then undergoes hydrolysis of any phosphorus-halogen bonds in a reaction which can be expressed as follows:

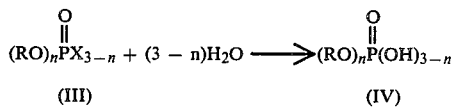

(III)              (IV)

Product IV, a multiphosphorus-containing ester is then reacted with an epoxide represented by the formula $_yR_2{=}O$ wherein y and $R_2$ are as defined above in a reaction which yields Product II:

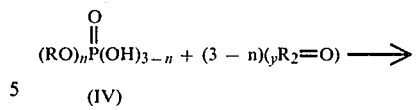

(IV)

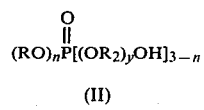

(II)

Suitable Lewis acid catalysts include magnesium chloride, stannic chloride, aluminum chloride, zinc chloride, and the like. The Lewis acid catalyst is used in an amount ranging from about 0.1 percent to about 3 percent by weight of the reaction mixture.

Suitable phosphorus oxyhalides include phosphorus oxychloride and phosphorus oxybromide.

The hydrolysis of any phosphorus-halide bond may be carried out by any method known to those skilled in the art.

Yet another process by which the compounds of the present invention can be produced involves the transesterification of a phosphate-containing or phosphonate-containing alcohol, represented by the formula ROH wherein R is as as defined above with a dialkyl phosphite represented by the general formula

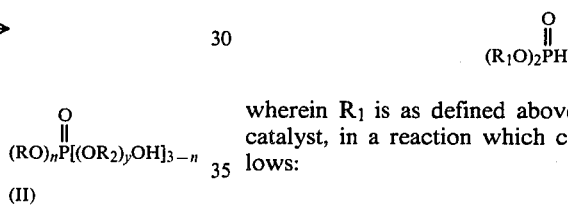

wherein $R_1$ is as defined above, in the presence of a catalyst, in a reaction which can be expressed as follows:

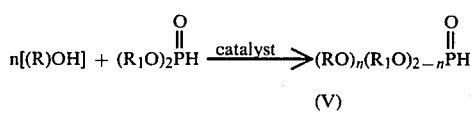

(V)

Product V, a phosphate-phosphite or phosphonate-phosphite results from the replacement of one or two simple alkyl groups by the phosphate-containing or phosphonate-containing alcohol.

Product V is then oxidized with oxygen and, for example, nitrogen dioxide, in a reaction as follows:

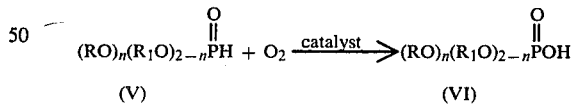

(V)                  (VI)

Product VI, a phosphoric acid derivative, is then reacted with an epoxide, represented by the formula $_yR_2{=}O$ wherein y and $R_2$ are, as previously defined, to yield the compound of Formula II:

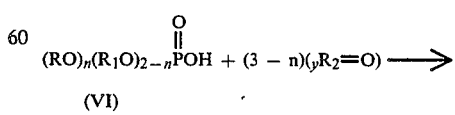

(VI)

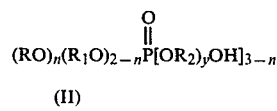

(II)

Suitable catalysts for the transesterification reaction of the phosphate-containing or phosponate-containing alcohol and the dialkyl phosphite include sodium methoxide, sodium ethoxide, and other alkoxide derivatives.

Suitable oxidants for the oxidation of the phosphate-phosphite or phosphonate-phosphite to the phosphoric acid include nitrogen dioxide and nitric oxide, or the oxidation can be done using oxygen in the presence of a nitride catalyst.

When a phosphate-containing or phosphonate-containing alcohol is reacted with phosphorus pentoxide, an amount ranging from about 1 to about 3 moles of the phosphate-containing or phosphonate-containing alcohol per mole of the phosphorus pentoxide, as $P_2O_5$, may be used.

When a phosphate-containing or phosphonate-containing alcohol is reacted with a phosphorus oxyhalide, an amount ranging from about 1 to about 3 moles of the phosphate-containing or phosphonate-containing alcohol per mole of the phosphorus oxyhalide may be used.

In a synthesis method wherein a phosphate-containing or phosphonate-containing alcohol is transesterified with a dialkyl phosphite, an amount ranging from about 1 to about 2 moles of the phosphate-containing or phosphonate-containing alcohol per mole of the dialkyl phosphite may be used.

The phosphate-containing or phosphonate-containing alcohols of the present invention may be synthesized by a variety of methods with one method of synthesis of a phosphonate-containing alcohol being the reaction of a dialkyl phosphite, represented by

with a formaldehyde derivative, such as a paraformaldehyde, in the presence of a catalyst, such as triethylamine. One example is the reaction of diethyl phosphite with paraformaldehyde in a 1:1 ratio in the presence of triethylamine as a catalyst:

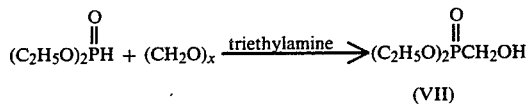

(VII)

Product VII, diethyl hydroxymethylphosphonate (DEHMP), is a suitable phosphonate-containing alcohol which can be used in the processes of the present invention.

If a phosphate-containing alcohol is used, this type of alcohol may be prepared by reaction of a dialkyl hydrogen phosphate with an oxirane compound. An example is the reaction of diethyl hydrogen phosphate with ethylene oxide:

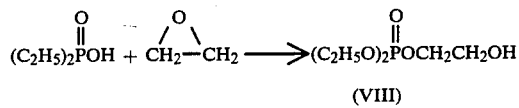

(VIII)

Compound VIII, diethyl hydroxyethyl phosphate, is a suitable phosphate-containing alcohol which may be used in the processes of the present invention.

Halogenated phosphate-containing and/or halogenated phosphonate-containing alcohols can also be used. Such alcohols may be synthesized by a number of reactions with one non-limiting example being the reaction of a tris(haloalkyl)phosphite with a hydrogen halide to produce a bis(haloalkyl)phosphite in a reaction which may be expressed as follows:

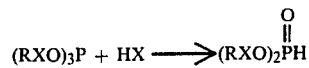

wherein R is an alkyl group of 1–20 carbon atoms and X is a halogen. The bis(haloalkyl)phosphite thus produced is then reacted with an aldehyde, such as paraformaldehyde, in a reaction as follows:

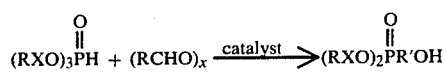

wherein R and R' are alkyl groups of 1–20 carbon atoms, and X is a halogen.

Non-limiting examples of suitable phosphonate-containing alcohols which may be used in these syntheses are:

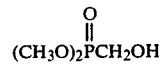

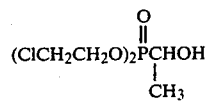

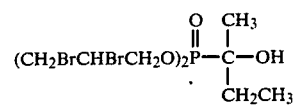

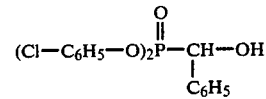

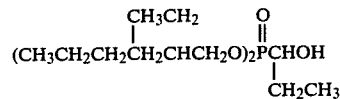

Non-limiting examples of suitable phosphate-containing alcohols which may be used in these syntheses are:

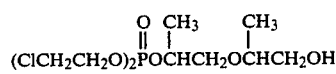

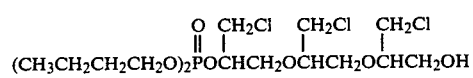

-continued

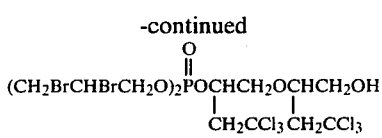

In addition to the above compounds, $R_1$, $R_3$, $R_5$, $R_6$ and $R_7$ can be suitable alkyl, haloalkyl, aryl and haloaryl groups such as, for example, methyl, ethyl, propyl, 2 chloroethyl, 2,3-dibromopropyl, butyl, octyl, phenyl, tolyl and p-chlorophenyl.

In addition to the above compounds, $R_6$ and $R_7$ can be suitable alkylene and haloalkylene groups derived from epoxides such as ethylene oxide, propylene oxide, butylene oxide, 4,4,4-trichlorobutylene oxide, epichlorohydrin, epibromohydrin and various glycidyl ethers.

Reaction of the phosphate-containing or phosphonate-containing alcohol with phosphorus pentoxide takes place readily, generally, by suspending the phosphorus pentoxide in an appropriate suspending fluid, such as toluene, and then adding the phosphate-containing or phosphonate-containing alcohol in an inert atmosphere.

Reaction of the phosphate-containing or phosphonate-containing alcohol with the phosphorus oxyhalide also takes place readily, generally, by slowly adding the phosphorus oxyhalide to a solution of the phosphate-containing or phosphonate-containing alcohol in the presence of an appropriate catalyst, or catalysts. Generally, the reaction is exothermic and if the exotherm is cooled too rapidly, additional heating may be necessary. Hydrolysis of any of the remaining phosphorus halide bonds can be accomplished by any method known to those skilled on the art.

The transesterification of a phosphate-containing or phosphonate-containing alcohol with a dialkyl phosphite also takes place readily, generally by mixing together the dialkyl phosphite and the phosphate-containing or phosphonate-containing alcohol in the presence of an appropriate catalyst, such as sodium methoxide with controlled vaporization of the departing alcohol. The reaction usually requires some heating. The oxidation is accomplished by gently bubbling in oxygen with sodium nitride with controlling of the exotherm produced.

Generally, it is preferable that the temperature of the reactions of the present invention be kept between 50° C. and 90° C. Thus, depending on the degree of exotherm seen, gradual cooling of the reaction mixture may be necessary.

Reaction of any of the phosphoric acid derivatives produced by the immediately aforementioned reactions with an oxirane, such as ethylene or propylene oxide, also takes place readily, generally by bubbling the oxirane, if it is in gaseous form, or adding the oxirane dropwise, if it is in liquid form, to the phosphoric acid derivative. Gradual heating is used to bring the reaction to completion and the gaseous oxirane, if such is used, can be stripped by any known technique such as sparging, etc.

It will be obvious to one skilled in the art that since the final product represented by Formula II itself contains alcohol functions, it may be reacted by any of the syntheses methods of the present invention to yield higher homologs.

Similarly, the stoichiometry of the general reactions can be adjusted so that the final phosphorus content, hydroxyl number and degree of hydroxyl functionality meets one's desired specifications.

The compounds of the present invention may be used for any purpose for which phosphorus compounds are suitable, with some non-limiting proposed examples of utility being:

1. As flame retardants for plastics such as polyurethanes, cellulosics, modified cellulosics, and polyesters.
2. As flame retardants for textiles such as cellulosics and polyesters.
3. As lubricant additives acting as a detergent, dispersive, corrosion inhibitor, and anti-erosion agents, anti-rust, extreme pressure additive and viscosity index improver.
4. As metal extractors, ore flotation agents.
5. As surfactants and emulsifying agents.
6. As chelants and sequestering agents.
7. Metal plating additives.

One particular use for the compounds of the present invention is to provide flame retardant properties to a number of combustible materials. An example is provided by the compound:

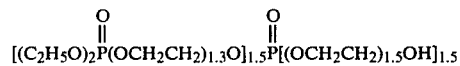

produced by any of the reactions of the present invention. The above compound, when incorporated into a flexible urethane foam formulation, imparts good flame retardant properties to the flexible urethane foam.

Another example is provided by the compound:

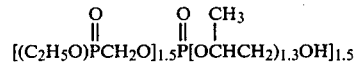

produced by any of the processes of the present invention. This compound, when used in a rigid foam formulation imparts flame retardant properties to the rigid urethane foam.

Another example is provided by the compound:

produced by any of the processes of the present invention. This compound, when used copolymerized with a trimethyl melamine derivative on 100% cotton flannel produced a fabric which exhibited flame retardant properties durable through ten detergent washings.

The present invention can comprise, consist of, or consist essentially of the following non-limiting examples.

EXAMPLE I

Preparation of Diethyl Hydroxymethylphosphonate

To a 2 liter, round bottomed flask fitted with a nitrogen inlet were added 500 grams (3.6 mole) of diethyl phosphite (Aldrich), 120 grams (3.8 mole) of paraformaldehyde (Baker) and approximately 6 milliliters of triethylamine. The mixture was stirred overnight at room temperature but no visible reaction had occurred so approximately 10 milliliters more of triethylamine was added and the mixture was slowly warmed to 90° C. The solution was heated for approximately an additional hour, filtered hot and distilled. 320 grams of a liquid product corresponding to a 60% yield was obtained.

EXAMPLE 2

Preparation of Diethyl Hydrogen Phosphate

A dry 2 liter, 3-necked flask was equipped with a fritted gas bubbler, condenser, nitrogen inlet, thermometer and magnetic stirrer. The air line into the flask contained, in sequence, a drying tube (DRIERITE ®+3A° sieve), a gas wash bottle containing 230 grams of nitrogen dioxide and a trap attached to the fritted gas bubbler. The flask was charged with 843 grams of diethyl phosphite, air was bubbled through the nitrogen dioxide and the nitrogen dioxide was, in turn, bubbled through the diethyl phosphite. After about 170 grams of nitrogen dioxide had vaporized into the solution, the vapor phase turned reddish-brown indicating that the reaction was nearly complete so dry air was bubbled in. The the mixture was then placed on a rotary evaporator and stripped for two hours at 60° C. at 5 millimeter Hg. The extracted compound had the following properties: 1.071 grams required 63.8 milliliters of 0.1N base to reach the methyl red end point, 1.071 grams of the compound required 6.3 milliliters of 0.1N base to reach the phenolphthalein end point.

EXAMPLE 3

Preparation of Diethyl Phosphonophosphoric Acid

A 2 liter, 3-necked flamed out flask was equipped with a mechanical stirrer, a dropping funnel, thermometer and reflux condenser. To this flask were added 70 grams (0.49 mole) of phosphorus pentoxide (MCB) and 380 grams reagent grade toluene (dried on a molecular sieve). Under a nitrogen atmosphere, diethyl hydroxymethylphosphonate (DEHMP) synthesized by the procedure of Example 1 was added dropwise with stirring. After about 35 minutes, a total of 260 grams (1.55 moles) of the DEHMP had been added. The solution was heated at 90° C. for 3 hours. The solution was then cooled, and placed on a rotary evaporator for 13 minutes. The final yield was 325 grams or 98% based on starting materials.

Titration with 0.1N base showed that 2.0 grams of the compound required 63.2 milliliters to the methyl red end point and 23.7 milliliters to the phenolphthalein end point, corresponding to the compound having 3.2 meg strong acid/g (theoretical=3.1) and 1.2 meg weak acid/g (theoretical=1.5). Further analytical data showed a compound of molecular weight 310 corresponding to an average formula of:

EXAMPLE 4

A 500 milliliter 3-necked flask was charged with 143 grams (0.46 mole) of the diethyl phosphonophosphoric acid produced by the method of Example 3 (previously titrated to methyl red end point showing an acid number of 177). The solution was warmed to 70° C. and 50 grams of ethylene oxide (Matheson) was gradually bubbled in. After the exotherm ceased, the solution was heated to 90° C. with refluxing of the ethylene oxide for 45 minutes. The ethylene oxide was then stripped yielding 118.1 grams of a water white oil. The molecular weight of the compound was 357 corresponding to an average formula of:

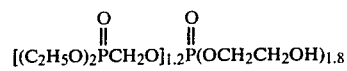

The calculated phosphorus percentage was 19%. The calculated OH number was 284. For titration, 2 grams of the compound were stirred into 0.1N HCl (10.0) milliliters. 17.9 milliliters of NaOH were required to the methyl red end point.

EXAMPLE 5

Similar to Example 4 except about 70 grams of propylene oxide was added dropwise to the acid (acid number=177). 196.2 grams of a water white material was obtained. Acid number=1.2 to a para-naphthol benzein (PNB) end point. The compound had an average formula:

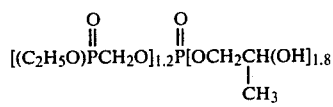

For titration 2.0 grams were stirred into 10.0 milliliters of 0.1N HCl for 10 minutes. 34.2 milliliters of 0.1N NaOH were required to the methyl red end point. HCl number=6.7

EXAMPLE 6

Synthesis of Diethyl Hydroxyethyl Phosphate

A 2 liter, 3-necked flask was equipped with a Dewar condenser, gas inlet and stirring bar. 875 grams (5.7 mole) of diethyl hydrogen phosphate was placed into the flask and about 400 grams of ethylene oxide were added over a 4 hour period. When the exotherm slowed, (pot temperature 50° C.) acid number=70. After the exotherm ceased and temperature dropped to 40° C., acid number=about 50. After refluxing of the ethylene oxide at 50° C. for 1 hour, acid number=about 18, after 3 hours at 50° C. acid number=about 7. All the above acid numbers were based on methyl red end point titration. The total yield was 1171 grams. Approximately half of the product was then wipe film distilled at 80° C. and 0.5 millimeter Hg. NMR data showed a compound having the formula:

acid number=1.7 to methyl red, 6.7 to PNB HCl acid to methyl red=14.3 to phenolphthalein=16.3 H$_2$O acid number=4.8 to methyl red HCl/H$_2$O acid number=12.6 to methyl red Thus, the compound had the structure

EXAMPLE 7

Into a 500 milliliter round bottom 3-necked flask was placed 32.7 grams (0.23 mole) of phosphorus pentoxide and 100 grams of toluene. 108 grams (0.69 mole) of diethyl hydroxyethyl phosphate produced according to the method of Example 6 was added dropwise over a period of 3 minutes with vigorous stirring. The solution was warmed for 2 hours at 80° C. followed by stripping. There was obtained 140 grams of a compound of an average formula:

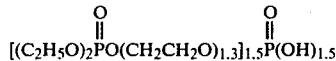

EXAMPLE 8

133 grams (0.435 mole) of the phosphatophosphoric acid obtained by the procedure of Example 7 were placed into a 3-necked, round bottom flask equipped with a Dewar condenser, gas inlet and magnetic stirrer. The solution was warmed to 50° C. and ethylene oxide was added at a controlled rate so that the temperature remained at 50°–55° C. with some ice cooling. After the exotherm ceased, excess ethylene oxide was added. The solution was stripped on a rotary evaporator at 10 millimeters Hg and 50° C. 182 grams of a light yellow viscous liquid was obtained. Titration results showed acid number H$_2$O →methyl red 1.7 mg KOH/g toluene-isopropanol→PNB 1.4 mg KOH/g The compound had an average approximate formula:

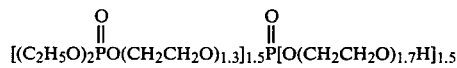

EXAMPLE 9

261 grams (1.23 mole) of diethyl hydroxyethylphosphate prepared by the method of Example 6 was placed in a 1 liter round bottomed flask with 150 milliliters of toluene and 58 grams (0.41 mole) of phosphorus pentoxide was added. The exotherm was controlled by the use of an ice bath. When the exotherm ceased, the solution was heated for 1 hour at 80° C. The heat was removed and 125 grams (2.8 moles) of ethylene oxide was added with cooling till the exotherm ceased. The solution was refluxed for 1 hour at which point Acid number=about 2 [(KOH:isopropanol:toluene)=2.7 milliliters 0.1N base for a 2.5 gram sample]. Ethylene oxide was then refluxed for 4 hours, at which point Acid number=about 1 [(KOH:isopropanol:toluene) 0.4 milliliters of 0.1N base for 2.5 grams sample]. The solution was then placed on a rotary evaporator at 60° C. at 10 millimeters Hg. There was obtained 400 grams of a compound having the formula:

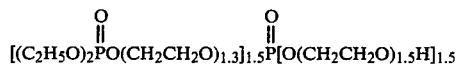

The calculated molecular weight was 487. Calculated % P was 15.9, calculated OH number=173, KOH acid number=0.8 mg KOH/g.

EXAMPLE 10

To a 1 liter, 3-necked round bottomed flask equipped with a thermometer, nitrogen inlet, mechanical stirrer and dropping funnel was added 44.7 grams (0.31 mole) of phosphorus pentoxide dissolved in 50 milliliters of toluene. To the flask was then added slowly 168 grams (0.31 mole) of DEHMP in 100 milliliters of toluene. The mixture was heated to 70° C. to 80° C. for 2 hours and then allowed to cool to room temperature. The solution was stripped on a rotary evaporator at 10 mm Hg at 90° C. 2.0 grams of the intermediate required 58.5 milliliters of 0.1N NaOH to methyl red end point and 10.5 milliliters to phenolphthalein end point.

To 192 grams (0.5 mole) of the above intermediate was added 90 grams (2 mole) of ethylene oxide. After all the ethylene oxide had been added, the solution was stripped on a rotary evaporator at 15 mm Hg at 50° C. Analytical results showed:
%P=19.4
OH#=160
Acid#=4.6

The compound had the average formula:

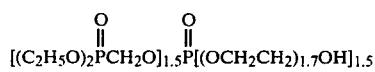

Examples 11–13 illustrate the synthesis of a halogenated phosphate-containing or phosphonate-containing phosphate ester of the present invention.

EXAMPLE 11

Preparation of Bis(Betachloroethyl)Phosphite

Into a 1 liter 3-necked flask equipped with a reflux condenser, mechanical stirrer, thermometer, and nitrogen inlet was added 500 grams (1.85 mole) of tris(betachloroethyl)phosphite and 75 grams (0.91 mole) of phosphorous acid. The mixture was heated to 80°–90° C. for about 1.5 hours. The ASTM acid# of the compound was 2.0.

EXAMPLE 12

Preparation of Bis(Betachloroethyl)Hydroxymethylphosphate

By reacting 375 grams (1.81 mole) of the bis(betachloroethyl)phosphite of Example 11 with 60 grams (1.9 mole) of paraformaldehyde in the presence of 30 grams of triethylamine, the bis(betachloroethyl) hydroxymethylphosphonate compound was produced.

EXAMPLE 13

To a 1 liter, 3-necked round bottomed flask equipped with a reflux condenser, thermometer and magnetic stirrer was added 91 grams (0.384 mole) of the bis)betachloroethyl)hydroxymethylphosphonate of Example 12, 100 grams of toluene and 18.2 grams (0.128 mole) of phosphorus pentoxide. The solution was heated at reflux for 1 hour and then cooled to 25° C. 30 grams of propylene oxide was added, the exotherm was allowed to cease, and an additional 20 grams of propylene oxide was added. The solvent was removed and the remaining solution was wipe film distilled at 1 mm Hg. The final ASTM acid# was 0.3. The compound had the average formula:

EXAMPLE 14

This example illustrates the reaction of a phosphorus oxyhalide with a phosphate-containing or phosphonate-containing alcohol.

To a 1 liter, 3-necked, round bottomed flask equipped with a mechanical stirrer, thermometer, H$_2$O condenser, a nitrogen inlet over the outlet of condenser to drying tube and an addition funnel were added 200 milliliters of 1,2-dichloroethane, 168 grams (1.2 mole) of diethyl hydroxymethylphosphonate synthesized by the procedure of Example 1, 105 grams of triethylamine and 2 grams of magnesium chloride. 4.9 grams (0.35 mole) of phosphorus oxychloride was added to the addition funnel. The 3-necked flask was heated to 80° C. and the addition of the phosphorus oxychloride was started. The exotherm was cooled in a water bath and the solution was heated again. After complete addition of the phosphorus oxychloride (15–20 minutes) infrared spectra showed a strong OH peak so the solution was heated an additional 3 hours. At termination, 400 cc of 1,2-dichloroethane was added, the mixture was washed once with 500 cc of 1N HCl, then twice with 500 cc H$_2$O followed by 500 cc of 0.5N NaOH and finally twice with 500 cc H$_2$O. The solution was dried over MgSO$_4$ and then placed on a rotary evaporator at 50° C. at 10 millimeters Hg. Acid number = <0.1 mg KOH/g. The compound had an average formula:

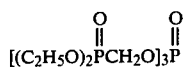

and was tris(diethylmethylphosphonate)phosphate.

EXAMPLE 15

315 grams (1.9 mole) of diethylhydroxymethylphosphonate (acid number=0.3) prepared by the process of Example 1, 300 grams (2.2 moles) of diethyl phosphite (Stauffer), and 2 grams (25%) in methanol of sodium methoxide were added to a 2 liter round bottomed flask which was equipped with a thermometer and Vigreaux column leading to a dry ice trap and Drierite ® trap and aspirator. The solution was warmed to 40° C. for 1 hour at 20 millimeters Hg. Volatiles collected in the dry ice trap. After 115 milliliters of volatiles had been collected, the solution was placed in a rotary evaporator. The compound produced is then placed in a 250 milliliter 3-necked, round bottom flask and oxygen and nitric oxide are bubbled in simultaneously. Alternatively, the oxygen and nitric oxide can be mixed in the Y tube and then bubbled into the mixture.

EXAMPLE 16

The composition produced according to Example 9,

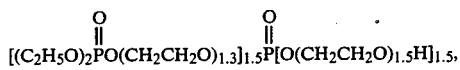

was incorporated at 12 p.h.r. into a flexible polyurethane foam having the following formulation:

|  | Parts by Weight |
| --- | --- |
| Polyol | 1.0 |
| Silicone surfactant | 1.0 |
| Water | 4.0 |

|  | Parts by Weight |
| --- | --- |
| Amine catalysts | 0.50 |
| Stannous octoate | 0.25 |
| Toluene diisocyanate | 55.1 |

The foam mixture was poured into an open-top box and allowed to expand into a 15 inch square block. It was then oven cured at 130° C. for about 10 minutes. This was followed by ambient temperature curing for 3 days.

Flammability testing was conducted pursuant to the Motor Vehicle Safety Standard 302 (MVSS-302). A control foam of the same formulation without the flame retardant was also prepared and tested for flammability.

In the MVSS-302 test, a specimen of foam 4 inches x ½ inch thick by 14 inches long is held horizontally between 2 V-shaped brackets which allows free access of air above and below. The specimen is ignited by a bunsen burner and the burning rate in inches per minute is measured. A burn rate below 4 inches/minute is usually required.

General Motors Corporation uses the following qualitative measures under MVSS-302.

| Does not ignite | DNI |
| --- | --- |
| Self-extinguishes (SE) before first mark (before 1½ inch total) | SE |
| SE in less than 3½ inches total | SE/NBR |
| SE after 3½ inches from starting point | SE, alpha burn rate |
| Burns full length | burn rate |

| The flammability results were as follows: | | |
| --- | --- | --- |
| MVSS-302 | Control | FLAME RETARDED FOAM |
| Initial Rating | Burn | SE |
| Avg. inch burned | 11.50 | — |
| Avg. sec. burned | 130.00 | — |
| Burn rate | 4.63 | — |
| DHA # rating | Burn | SE |
| Avg. inch burned | 9.90 | — |
| Avg. sec. burned | 107.89 | — |
| Burn rate | 4.92 | — |

*Dry heat average for 22 hours at 140° C.

Since the samples self-extinguished after the first flame application, the samples were given a SE rating.

EXAMPLE 17

By changing the formulation of the foam produced by following the procedure of Example 16, a rigid polyurethane foam can be produced. Also by following the procedure of Example 16, a compound of the present invention can be incorporated as a flame retardant additive into a rigid polyurethane foam.

EXAMPLE 18

The hydroxyethoxyphosphonophosphate produced by the procedure of Example 10 was tested as a flame retardant for textiles. The padding bath for the textiles tested was prepared according to the procedure set forth in U.S. Pat. No. 3,746,572, the subject matter therein being incorporated by reference. The treated textiles were tested for flammability resistance by the Department of Commerce (DOC) FF3-71 flammability test. Particulars of this test are available from the Department of Commerce. The samples were tested after hot washes (HW) and after 5 detergent washes (DW). The number of inches burned was measured with burned entire length (BEL) being an unacceptable flame retardant for the particular textile. As can be seen from TABLE I, the compound produced excellent results as a flame retardant for 100 percent cotton flannel.

TABLE I

| Experiment # | % Solid | 1 | 2 | 3 | 4 |
|---|---|---|---|---|---|
| Water | — | 39.1 | 18.9 | 59.4 | 45.9 |
| Surfactant (Triton X100) | 10 | 0.1 | 0.1 | 0.1 | 0.1 |
| Hydroxyethoxy Phosphonophosphate[1] | 100 | 31.5 | 31.5 | 21 | 21 |
| Aminoplast (Aerotex M3) | 80 | 76.3 | | 17.5 | |
| Zinc nitrate Catalyst (X4) | 25 | 3 | | 2 | |
| NMA | 60 | | 34.5 | | 23 |
| Potassium Dithionite | 5 | | 15 | | 10 |
| Fabric: | | 50% polyester/50% cotton | | 100% cotton | |
| Dry conditions °F./min. | | 250/3 | | 250/2 | |
| Cure conditions °F./min. | | 350/3 | | 350/2 | |
| Weight before padding (bond dry-5 min.) | | 23.0 | 23.0 | 15.7 | 16.3 |
| Weight after padding | | 42.6 | 42.3 | 34.2 | 34.5 |
| % Wet pick-up | | 85.2 | 84.0 | 118 | 111 |
| Weight after cure (before HW) | | 31.8 | 31.9 | 21.0 | 21.4 |
| % Add-on (before HW) | | 38.2 | 38.4 | 34.0 | 30.9 |
| Theoretical % add-on (before HW) | | 44.7 | 43.8 | 41.3 | 38.9 |
| Weight after 1 HW (bone dry-10 min.) | | 29.9 | 29.2 | 20.5 | 20.5 |
| % Add-on (after HW) | | 30.0 | 26.9 | 30.7 | 25.5 |
| % Retention after HW | | 78.5 | 70.1 | 90.3 | 82.5 |
| % Add-on (after 10 DW) | | 21.3 | | 21.0 | 10.7 |
| % Retention after 10DW | | 71.0 | | 68.4 | 42.0 |
| Overall retention | | 55.8 | | 61.8 | 34.6 |
| Hand: | | | | | |
| Before HW | | 5 | 4.5 | 5 | 4 |
| After HW | | 5 | 4 | 4 | 3 |
| After 10 DW | | 3 | | 3 | 2.5 |
| Color: | | | | | |
| Before HW | | off white | yellow | off white | lt. yellow |
| After HW | | off white | | off white | lt. yellow |
| After 10 DW | | off white | | off white | lt. yellow |
| Flame test FF3-71 Before HW | | | | | |
| After HW | | 4.5 | BEL | 2.75 | 4.0 |
| After 10 DW | | BEL | | 4.5 | BEL |

[1] 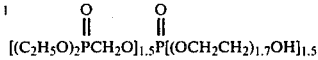

Additional features of the preferred and most preferred embodiments of the present invention are found in the claims hereinafter:

What is claimed is:

1. A compound of the formula:

$$(RO)_2P(OR_2)_yOH$$

wherein R is:

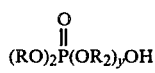

$R_8$ is the same or different and is alkyl, haloalkyl, aryl or haloaryl;

$R_2$ and $R_4$ are the same or different and are alkylene or haloalkylene;

Y is an integer from 1–10; and

Z is an integer from 1–10.

2. The compound of claim 1 wherein $R_1$ and $R_3$ are $C_1$–$C_{20}$ alkyl, haloalkyl, aryl or haloaryl.

3. The compound of claim 1 wherein $R_2$ and $R_4$ are $C_1$–$C_{20}$ alkylene or haloalkylene.

4. The compound of claim 1 wherein $R_3$ is ethyl.

5. The compound of claim 1 wherein $R_2$ or $R_4$ is an ethylene derivative.

6. The compound of claim 1 wherein $R_3$ is methyl.

7. The compound of claim 1 wherein $R_2$ or $R_4$ is propylene.

8. A compound of the formula:

wherein R is:

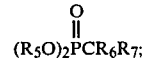

$R_1$ and $R_5$ are the same or different and are alkyl, haloalkyl, aryl or haloaryl;

$R_6$ and $R_7$ are the same or different and are hydrogen, alkyl, haloalkyl, aryl or haloaryl;

$R_2$ is alkylene or haloalkylene, alkylene or haloalkylene;

n is an integer from 1–2;

a is 0 or 1; and y is an integer from 1–10.

9. The compound of claim 8 wherein $R_1$ and $R_5$ are $C_1$–$C_{20}$ alkyl, haloalkyl, aryl or haloaryl.

10. The compound of claim 8 wherein $R_6$ and $R_7$ are $C_1$–$C_{20}$ alkyl, haloalkyl, aryl or haloaryl.

11. The compound of claim 8 wherein $R_6$ or $R_7$ is hydrogen.

12. The compound of claim 8 wherein $R_2$ is $C_1$–$C_{20}$ alkylene or haloalkylene.

13. The compound of claim 8 wherein $R_5$ is ethyl.

14. The compound of claim 8 wherein $R_6$ or $R_7$ is ethyl.

15. The compound of claim 8 wherein $R_2$ is an ethylene derivative.

16. The compound of claim 8 wherein $R_5$ is methyl.

17. The compound of claim 8 wherein $R_6$ or $R_7$ is methyl.

18. The compound of claim 8 wherein $R_2$ is propylene.

* * * * *

UNITED STATES PATENT AND TRADEMARK OFFICE
CERTIFICATE OF CORRECTION

PATENT NO. : 4,697,030
DATED : September 29, 1987
INVENTOR(S) : Thomas A. Hardy et al.

It is certified that error appears in the above-identified patent and that said Letters Patent is hereby corrected as shown below:

Col. 2, line 17 and Col. 5, line 2, "phosponate-containing" should read -- phosphonate-containing --;

Col. 2, line 64, the formula "$(R_5O)_2 \overset{O}{\underset{\|}{P}} CR_6R_7$"

should read -- $(R_5O)_2 \overset{O}{\underset{\|}{P}} CR_6R_7$ --;

Col. 4, line 26, "as as" should read -- as --;

Col. 4, line 65, the formula

"$(RO)_n(R_1O)_{2-n} \overset{O}{\underset{\|}{P}} [\overline{O}R_2)_y O\underline{H}]_{3-n}$"

should read -- $(RO)_n(R_1O)_{2-n} \overset{O}{\underset{\|}{P}} [(\overline{O}R_2)_y O\underline{H}]_{3-n}$ --;

Col. 5, line 59, the formula " $(C_2H_5)_2 \overset{O}{\underset{\|}{P}} OH$ " should read -- $(C_2H_5O)_2 \overset{O}{\underset{\|}{P}} OH$ --;

UNITED STATES PATENT AND TRADEMARK OFFICE
CERTIFICATE OF CORRECTION

PATENT NO. : 4,697,030

DATED : September 29, 1987

INVENTOR(S) : Thomas A. Hardy et al.

It is certified that error appears in the above-identified patent and that said Letters Patent is hereby corrected as shown below:

Col. 8, line 37, the formula

"$[(C_2H_5O)\overset{O}{\overset{\|}{P}}CH_2O]_{1.5}\overset{O}{\overset{\|}{P}}[\overset{CH_3}{\overset{|}{O}CH}CH_2)_{1.3}OH]_{1.5}$" should read --$[(C_2H_5O)_2\overset{O}{\overset{\|}{P}}CH_2O]_{1.5}\overset{O}{\overset{\|}{P}}[(O\overset{CH_3}{\overset{|}{C}H}CH_2)_{1.3}OH]_{1.5}$--;

Col. 8, line 47, the formula

"$[(C_2H_5O)\overset{O}{\overset{\|}{P}}CH_2O]_{1.5}\overset{O}{\overset{\|}{P}}[(OCH_2CH_2)_{1.7}OH]_{1.5}$"

should read

--$[(C_2H_5O)_2\overset{O}{\overset{\|}{P}}CH_2O]_{1.5}\overset{O}{\overset{\|}{P}}[(OCH_2CH_2)_{1.7}OH]_{1.5}$--;

Col. 9, line 20, "the" after "The" should be deleted;

UNITED STATES PATENT AND TRADEMARK OFFICE
CERTIFICATE OF CORRECTION

PATENT NO. : 4,697,030

DATED : September 29, 1987

INVENTOR(S) : Thomas A. Hardy et al.

It is certified that error appears in the above-identified patent and that said Letters Patent is hereby corrected as shown below:

Col. 10, line 24, the formula

"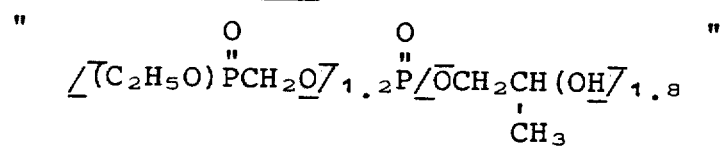"

should read

--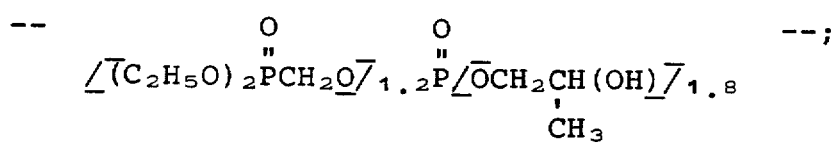--;

Col. 12, line 53, "bis)beta-" should read -- bis(beta- --;

Col. 14, line 39, "DHA#" should read -- DHA* --;

Col. 15, line 30, Table I, for Experiment #2, -- yellow -- should appear for the "Color" observation "After HW" --;

Col. 15, line 53, in Claim 1, "$R_8$" should read -- $R_3$ --;

UNITED STATES PATENT AND TRADEMARK OFFICE
CERTIFICATE OF CORRECTION

PATENT NO. : 4,697,030

DATED : September 29, 1987

INVENTOR(S) : Thomas A. Hardy et al.

It is certified that error appears in the above-identified patent and that said Letters Patent is hereby corrected as shown below:

<u>Col. 16, line 40,</u> the formula $$"\quad (R_5O)_2 \overset{\overset{O}{\|}}{P} CR_6R_7 \quad "\quad \text{should read} \quad -- \quad (R_5O)_2 \overset{\overset{O}{\|}}{P}\diagup CR_6R_7 \quad --; \text{ and}$$

<u>Col. 16, lines 46-47,</u> the recitation "alkylene or haloalkylene" (second occurrence) should be removed.

Signed and Sealed this

Sixteenth Day of February, 1988

Attest:

DONALD J. QUIGG

*Attesting Officer*   *Commissioner of Patents and Trademarks*